United States Patent [19]
Masuda et al.

[11] Patent Number: 5,853,406
[45] Date of Patent: Dec. 29, 1998

[54] PASSIVE DRUG DELIVERY APPARATUS

[75] Inventors: Kouichirou Masuda, Kashiwara; Kazumasa Maeda, Kadoma; Haruki Kazama, Musashino, all of Japan

[73] Assignee: Baxter International Inc., Deerfield, Ill.

[21] Appl. No.: 704,223

[22] Filed: Aug. 23, 1996

[30] Foreign Application Priority Data

Aug. 24, 1995 [JP] Japan .................................. 239270/95

[51] Int. Cl.⁶ .................................................. A61M 5/00
[52] U.S. Cl. ............................................. 604/414; 604/85
[58] Field of Search .......................... 604/28, 49, 82–88, 604/408–416

[56] References Cited

U.S. PATENT DOCUMENTS

| | | |
|---|---|---|
| 4,804,366 | 2/1989 | Zdeb et al. . |
| 4,832,690 | 5/1989 | Kuu . |
| 4,850,978 | 7/1989 | Dudar et al. . |
| 4,874,366 | 10/1989 | Zdeb et al. . |
| 4,936,829 | 6/1990 | Zdeb et al. . |
| 5,024,657 | 6/1991 | Needham et al. . |
| 5,049,129 | 9/1991 | Zdeb et al. . |
| 5,074,844 | 12/1991 | Zdeb et al. . |
| 5,167,642 | 12/1992 | Fowles . |
| 5,226,900 | 7/1993 | Bancsi et al. . |
| 5,356,380 | 10/1994 | Hoekwater et al. . |
| 5,385,547 | 1/1995 | Wong et al. . |
| 5,429,614 | 7/1995 | Fowles et al. . |
| 5,484,406 | 1/1996 | Wong et al. . |
| 5,501,676 | 3/1996 | Niedospial et al. ..................... 604/414 |
| 5,547,471 | 8/1996 | Thompson et al. . |
| 5,649,907 | 7/1997 | Mori et al. ............................... 604/414 |

FOREIGN PATENT DOCUMENTS

| | | |
|---|---|---|
| 9501133 | 1/1995 | WIPO . |
| 9501196 | 1/1995 | WIPO . |

*Primary Examiner*—William Lewis
*Attorney, Agent, or Firm*—Mark J. Buonaiuto; Jeffrey C. Nichols; Paul E. Schaafsma

[57] ABSTRACT

The present invention provides a passive drug delivery apparatus which has a simplified structure. The present invention includes a junction member, disposed within the fluid conduit, for forming a first flow path to supply a medical liquid along the fluid conduit. A coupling member is provided, one end of which is to be coupled to the junction member, and the other end of which is to be inserted into a vial containing a beneficial agent. The coupling member includes structure to close the medical liquid flow path, a second flow path for introducing the medical liquid into the vial and a third flow path for delivering the mixed solution containing the medical liquid and agent.

9 Claims, 6 Drawing Sheets

PASSIVE DRUG DELIVERY APPARATUS

FIELD OF THE INVENTION

This invention relates to a passive drug delivery apparatus used in conjunction with an administration set in which a beneficial agent is reconstituted through a medical liquid delivered to a patient.

BACKGROUND OF THE INVENTION

Administration sets for intravenously administering a liquid, generally called a transfusion liquid, and sometimes containing a dextrose solution, a solution of salt or water (hereinafter called a medical liquid) are widely used. In such a set a particular drug is frequently mixed with the medical liquid to be administered.

The administration set generally comprises a container containing a large volume of medical liquid, a cylindrical instillator, flow rate control means, a fluid filter, means for removing air, an injection site for injecting additional drug mixture, fluid conduits for connection, and means for coupling inlet and outlet portions.

Conventionally, when the administration set is used to supply a patient with a medical liquid mixed with a particular agent, if the agent is not liquid, it is first liquefied by using a diluent or other agents and then infused into the injection site so that the agent is mixed with the medical liquid.

This method, however, carries a risk of various kinds of contamination that are attributable to the requirements for the work of infusing a drug into the medical solution and preparatory operations therefor.

Various countermeasures have been taken to avoid these risks, and to relieve the medical workers from the work.

Representatives of such countermeasures are described in Japanese Patent Publication Nos. 5-60758 and 5-81271. The system taught by these publications comprises disposing a vial-like drug container in the middle of a fluid conduit for a medical liquid, and passing the medical liquid through the drug container to deliver a mixed solution containing the medical solution and drug. This type of system is referred to as a passive drug delivery system.

In that system a socket or a receptacle and a cartridge to be coupled therewith are provided. The drug container is attached to the cartridge so that, when the cartridge is connected to the receptacle, the inside space of the drug container is made to communicate with the flow path of the medical solution.

In this passive drug delivery system once the drug container is docked into the cartridge, there is no chance for the drug in the container to be exposed to the air, and all the mixing operation is automatically carried out by the medical solution, so that very high safety can be secured, and so that the work of the operator can be saved.

However, in the conventional system a receptacle is previously disposed in the middle of a medical liquid flow path or fluid conduit. In operating the system, a cartridge is first set up by inserting a cannula into a drug container, and then the cartridge containing the cannula is docked to the receptacle to start the operation.

Such a conventional system uses precisely dimensioned components, all of which are designed to be continuously used as they are once the operation is started. While the use of the cannula especially secures an accurate operation, in manufacturing the cannula, there could be some problems such as a special consideration about quality control in manufacturing technique and cost.

What would therefor be advantageous is to provide an improved passive drug delivery apparatus, which can resolve the problems stated above by using materials or members easy to manufacture, while enjoying the advantages of the passive drug delivery system; that is, an apparatus wherein an interruption of drug delivery can freely be made if necessary, the manufacture and operation of which is simple.

SUMMARY OF THE INVENTION

In one aspect of the apparatus of this invention a junction member is provided disposed within the fluid conduit, for forming first flow path means to supply a medical liquid along the fluid conduit. A coupling member is further provided, one end of which is to be coupled to the junction member, and the other end of which is to be inserted into a vial containing the beneficial agent. The coupling member includes means for closing the medical liquid flow path, second flow path means for introducing the medical liquid into the vial, and third flow path means for delivering the mixed solution containing the medical liquid and agent.

In one embodiment of the present invention, the coupling part of the junction member is made of a pierceable plate so that the part is easily broken.

In another embodiment of the present invention, the coupling part of the junction member is made of a pierceable plate so that the part is easily broken, and screw threads are provided around the outside of the coupling part, so that a lid may be screwed on the threads.

In a further embodiment of the present invention, the coupling member has an overall "L" shape.

In a still further embodiment of the present invention, the coupling member has an exhaust opening.

In a further embodiment of the present invention, the coupling member has at the other end a vial holder.

BRIEF DESCRIPTIONS OF THE DRAWINGS

DETAILED DESCRIPTION OF A PREFERRED EMBODIMENTS

Preferred embodiments of this invention will now be detailed by reference to the attached drawings.

Figure 1:
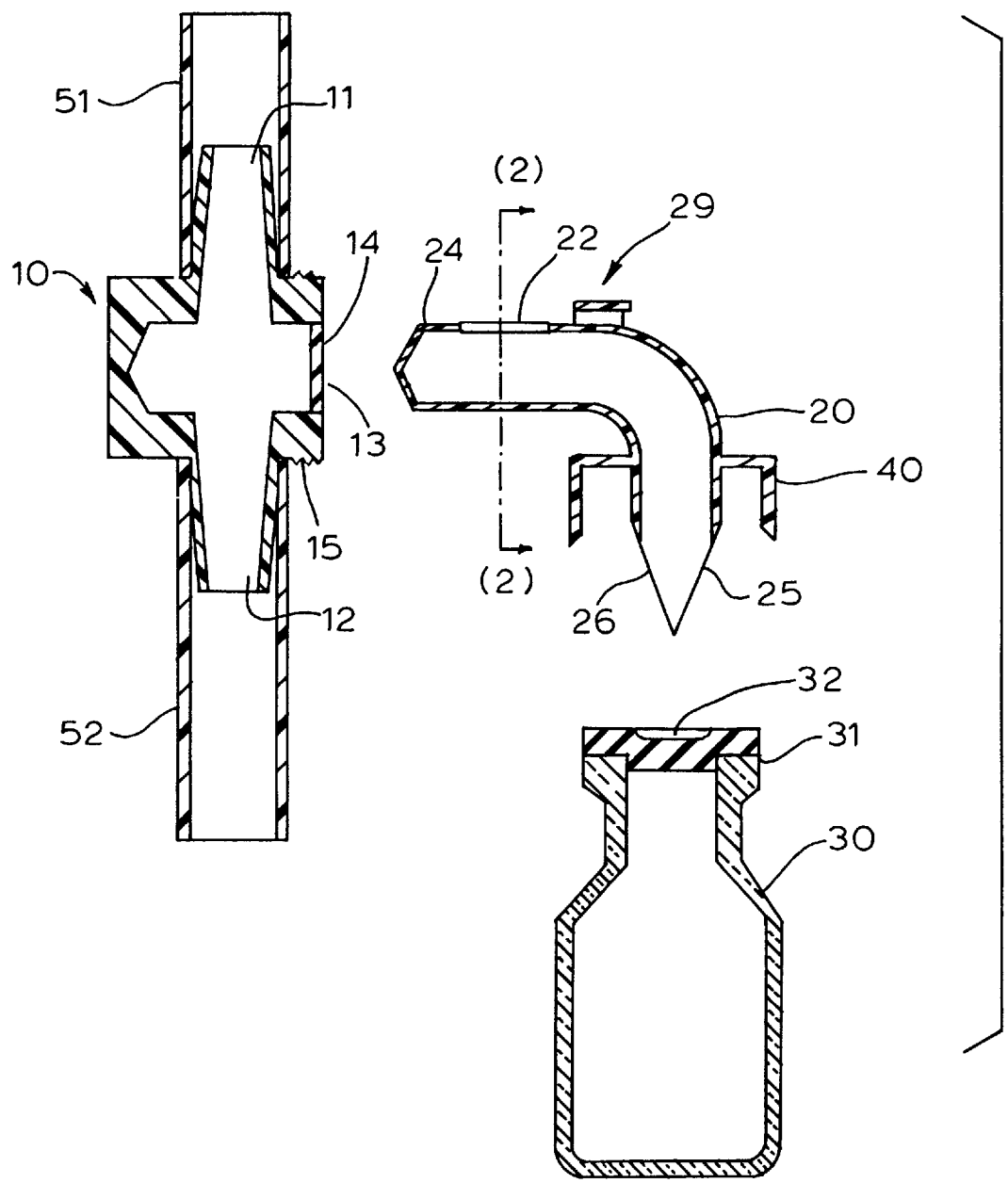
FIG. 1 is an overall schematic of the passive drug delivery apparatus made in accordance with the principles of the present invention.
Figure 2:
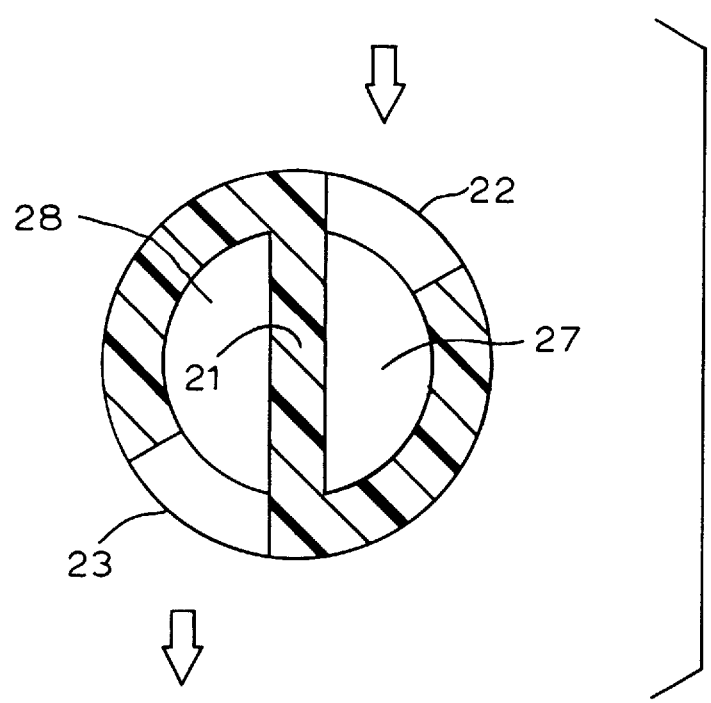
FIG. 2 is a sectional view of the drug delivery apparatus FIG. 1 indicated by taken at the line 2—2.
Figure 3:
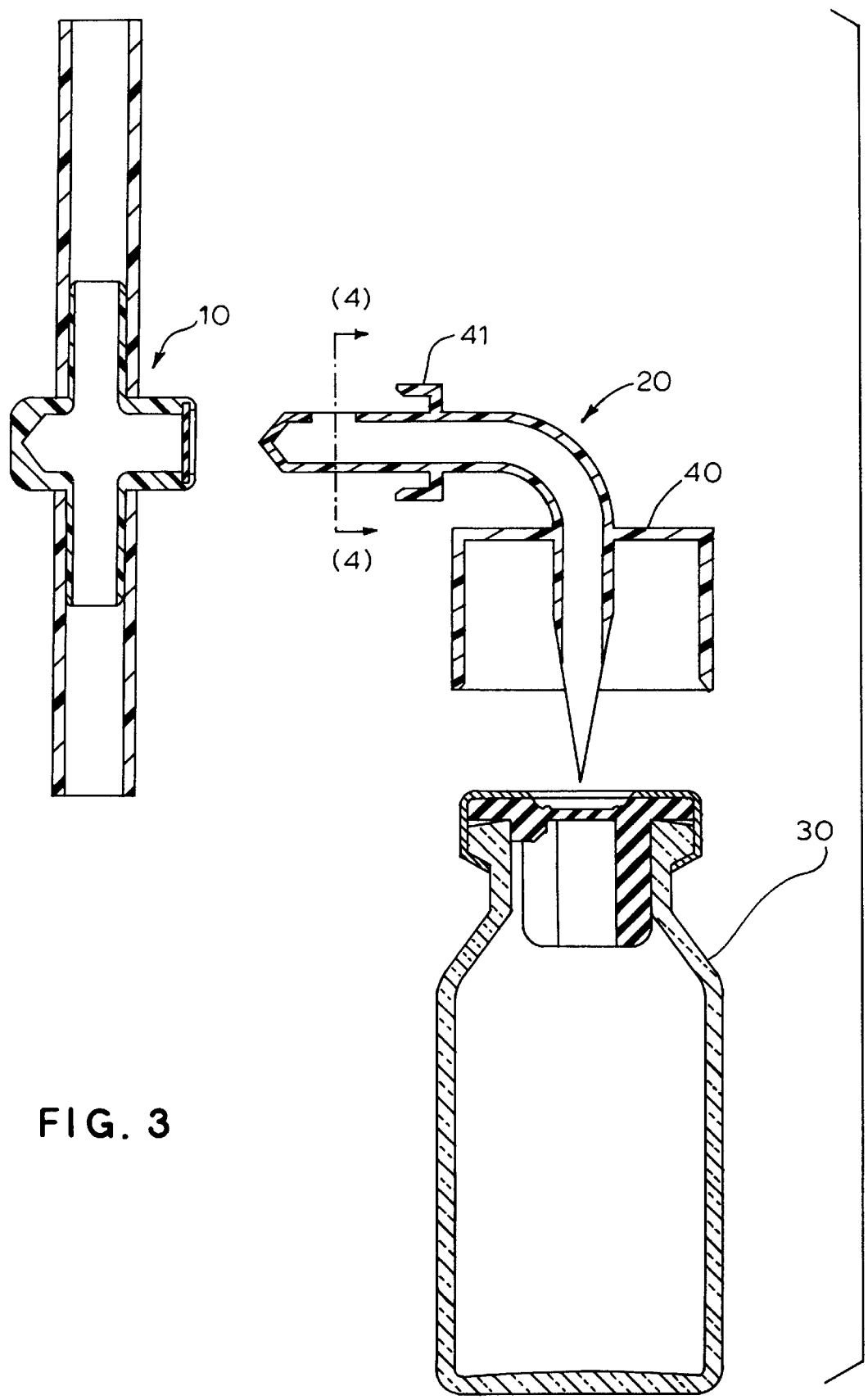
FIG. 3 is an overall schematic of another embodiment of a passive delivery apparatus made in accordance with the principles of the present invention.

FIG. 1 exemplifies an overall schematic of a passive drug delivery apparatus made in accordance with the principles of the present invention, and FIG. 2 shows a sectional view of the drug delivery apparatus of FIG. 1 in a direction and location indicated by the line 2—2 in FIG. 1.

The passive drug delivery apparatus of the present invention mainly comprises a junction member 10, coupling member 20, and a vial 30.

The junction member 10 is a cylindrical member having an inlet 11 and an outlet 12. The junction member 10 inserted between fluid conduits 51 and 52 for the medical solution to form a medical liquid flow path. The fluid conduit 51 is connected with a container (not shown) containing the medical liquid, while the fluid conduit 52 is to be connected to a patient, for example, via an intravenous injection member (not shown).

Through the coupling part 13, the junction member 10 is pierced by a coupling member 20 and is coupled with the coupling member 20. For this end, the coupling part 13 has a pierceable plate 14 made of a relatively breakable material. Screw threads 15 are provided around the outside of the coupling part 13 so that a lid is fitted onto the junction member when no delivery operation is performed.

The coupling member 20 to be coupled with the junction member 10 comprises means for interrupting the medical liquid flow path of the fluid conduit, and for forming first medical liquid flow path means, second flow path means for introducing the medical liquid into the vial, and third flow path means for delivering the mixed solution of the drug in the medical liquid. At one end of the coupling member 20, an end part or insert part 24 is provided which has the shape complimentary with its counterpart of a junction member such that, upon coupling, the medical liquid flow path of the fluid conduit perpendicular to the coupling member is interrupted, and a medical liquid introduction flow path 27 and a mixed solution delivery flow path 28 are formed by means of the coupling member 20. That is, the inside hollow of the coupling member 20 is divided by a partition 21 into two parts best seen in FIG. 2 so that the introduction flow path 27 having an introduction opening 22 and the delivery flow path 28 having an delivery opening 23 are formed, and the medical liquid can only pass through the introduction flow path 27. Although the coupling member may have any overall shape, it preferably has an L-like shape with a bend of 90 degrees.

The introduction opening 22 is provided near the end part 24 such that when the coupling member 20 is coupled with the junction member 10, the opening 22 is open to the medical liquid flow path of the junction member in communication with the medical liquid inlet 11. Thus, the introduction opening 22 of the introduction flow path 27 is generally provided on the upper half side of the coupling member 20.

The delivery opening 23 is provided near the end part 24 such that, when the coupling member 20 is coupled with the junction member 10, the delivery opening 23 is open to the medical liquid flow path of the junction member in communication with the medical liquid outlet 12. Thus, the delivery opening 23 of the delivery flow path 28 is generally provided on the lower half side of the coupling member 20.

On one side of the opposite end of the coupling member 20, at which the medical liquid introduction flow path 27 ends, an outlet 25 of the introduction flow path is provided.

Figure 4:
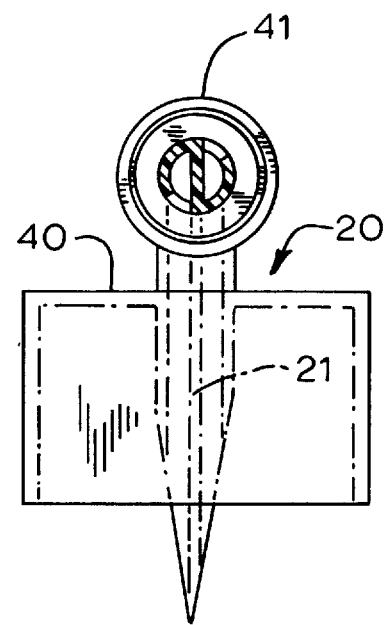
FIG. 4 is a sectional view of the drug delivery apparatus of FIG. 3 indicated by taken at the 4—4.

On the other side of the opposite end of the coupling member 20, at which the mixed solution delivery flow path 28 starts, an inlet 26 of the delivery flow path is provided. As shown in FIGS. 2 and 4, the introduction flow path 27 and the delivery flow path 28, provided within the coupling member 20, are separated by the central partition 21.

As needed, the coupling member 20 is provided with an exhaust opening 29. The exhaust is generally configured such that it is communicated with the delivery flow path 28, and it is permeable to gas but impermeable to liquid, and its positioning including its height and place can freely be selected.

The vial 30 has an opening part 31, at which a sealing part 32 is provided. That is, a drug is sealed within the vial 30 through the sealing part 32. When the drug in the vial 30 is to be used, the other end of the coupling member 20, provided with the outlet 25 of the medical liquid introduction flow path 27 and the inlet 26 of the mixed solution delivery flow path 28, is made to pierce through the sealing part 32 into the vial. A vial holder 40 is disposed near the other end of the coupling member 20, namely, near the outlet 25 of the introduction flow path and the inlet 26 of the delivery flow path, so that when the coupling member 20 is inserted into the vial 30, the coupling there between is secured. Since the coupling member 20 has a L-like shape with a bend of about 90 degrees, the vial is used with its opening part facing upwards.

Figure 5:
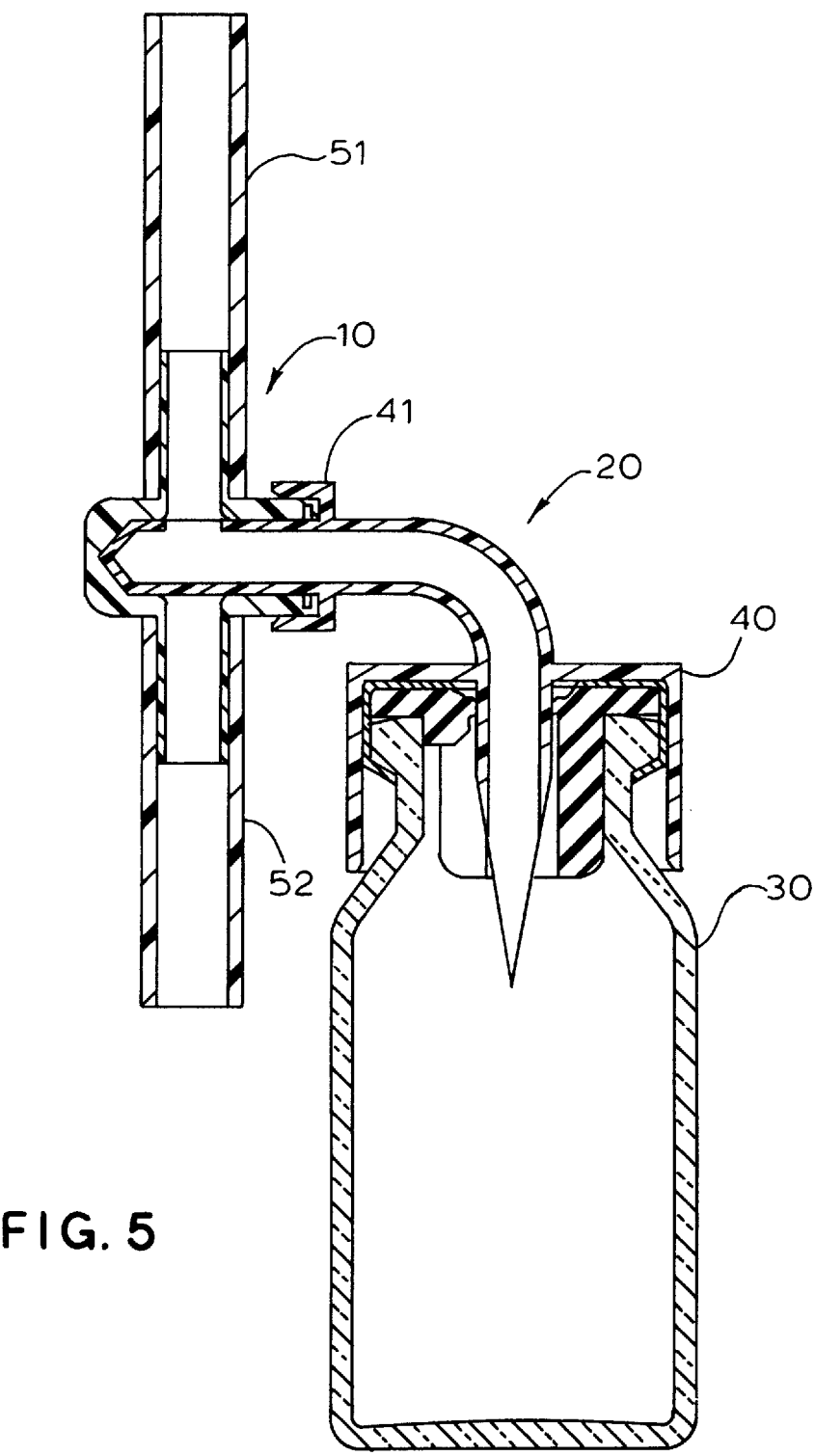
FIG. 5 is an overall schematic showing a use of the passive drug delivery apparatus made in accordance with the principles of the present invention.
Figure 6:
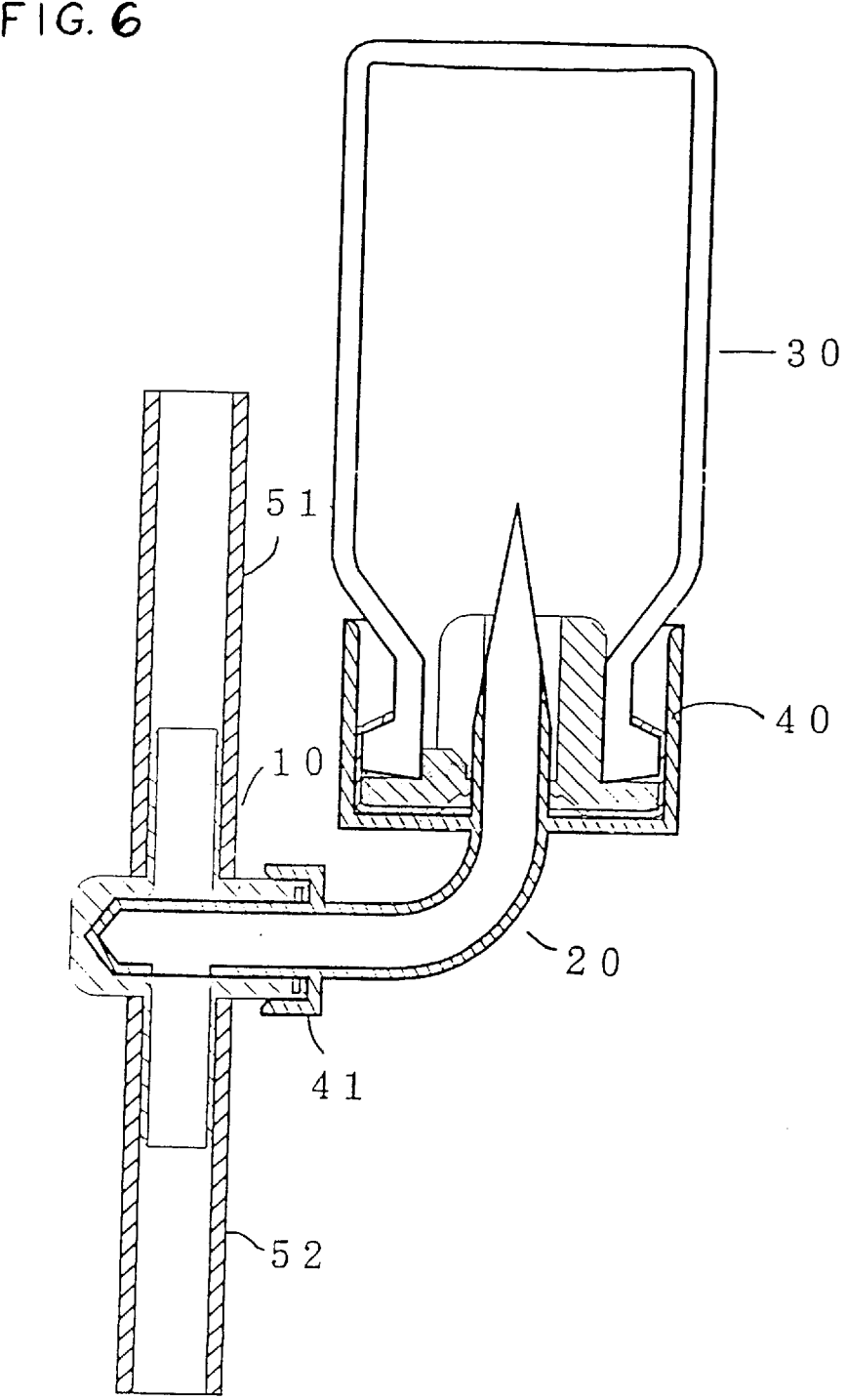
FIG. 6 is an overall schematic showing another use of the passive drug delivery apparatus made in accordance with the principles of the present invention.

As shown in FIGS. 5 and 6, the vial can be used with its opening part faced downwards when the supply of the medical liquid stops. As can be seen from the FIGS. 3–6, which show another embodiment of this invention, the configuration of the apparatus is substantially the same as that of FIG. 1 except that the coupling member 20 is rotatably coupled through a guide member 41 with the junction member 10 so that the outlet 25 of the introduction flow path and the inlet 26 of the delivery flow path can be shifted from the downward position to the upward position. In the apparatus of FIG. 5, when the medical liquid supply from the conduit 51 is stopped during a passive drug delivery operation, the mixed solution will remain within the vial. In such a case, when the coupling member 20 is rotated by 180 degrees as shown in FIG. 6 so that the opening part of the vial faces downwards, the mixed solution remaining in the vial flows through the medical liquid delivery flow path to the liquid conduit 52 due to the effect of the air entering into the vial through the mixed solution delivery flow path so as to discharge almost all the mixed solution remaining in the vial. Further, even if the medical liquid remains in the fluid conduit 51, the remaining mixed solution can substantially be purged by repeating the turning operation stated above while the conduit is closed.

When the operation of the coupling member 20 is to be stopped with the pierceable plate 14 of the junction member broken, it can be done just by closing the coupling part 13 with a lid (not shown) being fitted in the threads provided around the coupling part 13 after removing the coupling member 20 from the junction member 10.

In operating the passive delivery apparatus of this invention, a first preparatory step is to insert the junction member 10 between the medical liquid conduits.

In this state, the medical liquid conduit 51 is closed by a clip or the like, the coupling member 20 is coupled with the junction member 10 by making one end portion 24 pierce through the pierceable plate 14 of the junction member, and by making the other end of the coupling member pierce through the sealing part of the vial 30, thereby the preparatory steps are completed.

In this state, the operation can be started by removing the clip closing the medical liquid conduit 51. The medical liquid flows from the conduit 51 into the medical liquid supply flow path of the junction member 10, and then it flows from the introduction opening 22 of the coupling member 20 into the medical liquid introduction flow path 27. The medical liquid flows from the outlet 25 of the introduction flow path into the vial 30 to fill the inside thereof. At this time the medical liquid is mixed with the drug to provide a mixed solution.

Further, when the medical liquid is introduced into the vial, the mixed solution around the inlet 26 of the mixed solution delivery flow path 28 passes into the delivery flow path. The mixed solution passed into the delivery flow path progresses to the delivery opening 23, and from which opening it is supplied through the medical liquid outlet 12 to the fluid conduit 52 to be injected into the patient's body.

During the operation the vial 30 is securely connected by the vial holder 40 to the coupling member 20 so that there is no possibility for the vial to fall off. The medical liquid introduced into the vial is completely discharged since there is no flow path other than the medical liquid introduction flow path 27 and the mixed solution delivery flow path 28 therein. If the exhaust opening 29 is provided, unnecessary air will be easily exhausted out of the system. When the supply of the medical liquid stops, the remaining mixed solution in the vial can be purged by turning the coupling member 20 by 180 degrees so that the opening part of the vial faces downwards. After the completion of operation, the coupling member 20 is detached from the junction member 10 by pulling out one end portion 24 of the coupling member, and the coupling part 13 near the pierceable plate 14 is sealingly covered by a lid. In the apparatus of the present invention, the used vial can be removed and exchanged with a new one, so that a drug can be continuously introduced into the medical liquid as needed.

Thus, the present invention can perform all operation passively. Namely, a drug can be introduced into, mixed with, and delivered with the medical liquid automatically.

Although the apparatus of this invention has a simplified structure, it can attain the purposes without sacrificing the advantages of a passive drug delivery system, and has practical effects in preventing a drug from remaining in the vial, which is often the case with the conventional passive drug delivery system that needs complex and accurate mechanisms. Thus, this invention certainly enhances the usefulness of the passive drug delivery system. It should be understood that various changes and modifications preferred in to the embodiment described herein will be apparent to those skilled in the art. Such changes and modifications can be made without departing from the spirit and scope of the present invention and without demising its attendance advantages. It is therefore intended that such changes and modifications be covered by the appended claims.

What is claimed is:

1. An apparatus for the delivery of a passively reconstituted beneficial agent to a patient, the apparatus adapted to be disposed in the middle of a fluid conduit to supply a medical liquid, comprising:

a junction member adapted to be disposed within the fluid conduit, for forming a first flow path to supply the medical liquid through the fluid conduit, and a coupling member, one end of which is adapted to be coupled to the junction member, an the other end of which is adapted to be inserted into a vial containing the beneficial agent, said coupling member having means for closing the medical liquid flow path, a second flow path for delivering the medical liquid into the vial, and a third flow path for delivering the mixed solution containing the medical liquid and beneficial agent.

2. The apparatus of claim 1, wherein the coupling member of said junction member is made of a pierceable plate that is easily broken.

3. The apparatus of claim 2, further wherein a lid is provided, and screw threads are provided around the outside of said coupling member, so that the lid may be screwed on the threads.

4. The apparatus of claim 2, wherein said coupling member has an overall "L" shape, and is capable of rotating 180 degrees relative to the junction member.

5. The apparatus of claim 1, wherein said coupling member has an overall "L" shape, and further wherein the means for closing comprises means for rotating the coupling member 180 degrees relative to the junction member.

6. The apparatus of claim 5, wherein said coupling member has an exhaust opening.

7. The apparatus of claim 6 wherein said coupling member has at the end opposite the junction member a vial holder.

8. The apparatus of claim 1, wherein said coupling member has an exhaust opening.

9. The apparatus of claim 1 wherein said coupling member has at the end opposite the junction member a vial holder.

* * * * *